United States Patent [19]

Scherrer et al.

[11] Patent Number: 4,716,178

[45] Date of Patent: Dec. 29, 1987

[54] SUBSTITUTED DI-T-BUTYLPHENOLS

[75] Inventors: Robert A. Scherrer, White Bear; Mark A. Rustad, Afton, both of Minn.

[73] Assignee: Riker Laboratories, Inc., St.Paul, Minn.

[21] Appl. No.: 879,472

[22] Filed: Aug. 27, 1986

Related U.S. Application Data

[63] Continuation-in-part of Ser. No. 876,287, Jun. 17, 1986, abandoned, which is a continuation of Ser. No. 757,454, Jul. 22, 1985, abandoned.

[51] Int. Cl.$^4$ .................. A61K 31/195; C07C 101/34
[52] U.S. Cl. ...................... 514/563; 560/16; 560/43; 560/44; 560/110; 548/253; 562/431; 562/454; 514/535; 514/539; 514/562; 514/381
[58] Field of Search ............... 560/16, 43, 44, 110; 548/253; 562/431, 454; 514/535, 539, 562, 381, 563

[56] References Cited

U.S. PATENT DOCUMENTS

| 3,313,848 | 4/1967 | Scherrer et al. | 260/518 |
|---|---|---|---|
| 3,766,280 | 10/1973 | Carney et al. | 562/454 |
| 3,773,936 | 11/1973 | Shen et al. | 562/454 |
| 4,070,484 | 1/1978 | Harita et al. | 424/319 |
| 4,153,728 | 5/1979 | Wolff et al. | 514/563 |
| 4,172,151 | 10/1979 | Moore | 424/330 |
| 4,420,115 | 4/1984 | Ramsden et al. | 548/253 |
| 4,496,590 | 1/1985 | Schlegel et al. | 514/646 |
| 4,510,139 | 4/1985 | Bailey | 514/234 |
| 4,515,980 | 5/1985 | Bailey | 560/45 |
| 4,528,392 | 7/1985 | Mussen et al. | 562/454 |
| 4,568,684 | 2/1986 | Rentzece | 560/44 |

FOREIGN PATENT DOCUMENTS

| 181568 | 5/1986 | European Pat. Off. | |
| 2098587 | 10/1972 | France | 562/454 |

OTHER PUBLICATIONS

Derwent for Japanese Application 54758.
Goldstein et al., Helv. Acta. 11, 239-2451, (1928).

Primary Examiner—James H. Reamer
Attorney, Agent, or Firm—Donald M. Sell; James A. Smith; Robert W. Sprague

[57] ABSTRACT

Novel compounds which are 2,6-di-t-butylphenols substituted on the 4 position by an anilino group, which anilino group is substituted by a group which includes carboxyl, tetrazolyl or N-methyltetrazolyl are useful as inhibitors of leukotriene synthesis and as antiallergic agents. Pharmaceutical compositions containing such compounds and pharmacological methods for use of such compounds are also disclosed.

9 Claims, No Drawings

SUBSTITUTED DI-T-BUTYLPHENOLS

CROSS-REFERENCE TO RELATED APPLICATION

This application is a continuation-in-part of copending application Ser. No. 876,287 which was filed on June 17, 1986 now abandoned, which in turn is a continuation of application Ser. No. 757,454 which was filed on July 22, 1985, and is now abandoned.

TECHNICAL FIELD

This invention relates to compounds which inhibit leukotriene synthesis and are antiallergic agents. Pharmaceutical compositions comprising such compounds and pharmacological methods of using such compounds are also described.

BACKGROUND OF THE INVENTION

The leukotrienes are a novel group of biologically active mediators derived from arachidonic acid through the action of lipoxygenase enzyme systems. There are two groups of leukotrienes derived from the common unstable precursor Leukotriene $A_4$. The first of these are the peptido-lipid leukotrienes, the most important being Leukotrienes $C_4$ and $D_4$. These compounds collectively account for the biologically active material known as the slow reacting substance of anaphylaxis.

The leukotrienes are potent smooth muscle contracting agents, particularly on respiratory smooth muscle, but also on other tissues as well. In addition, they promote mucous production, modulate vascular permeability changes and are potent inflammatory mediators in human skin. The most important compound in the second group of leukotrienes, namely dihydroxy fatty acids, is Leukotriene $B_4$. This compound is a potent chemotactic agent for neutrophils and eosinophils and, in addition, may modulate a number of other functions of these cells. It also affects other cell types such as lymphocytes and, for example, may modulate the action of suppressor cells and natural killer cells. When injected in vivo, in addition to promoting the accumulation of leukocytes, Leukotriene B4 is also a potent hyperalgesic agent and can modulate vascular permeability changes through a neutrophil dependent mechanism. Both groups of leukotrienes are formed following oxygenation of arachidonic acid through the action of a lipoxygenase enzyme. See for example, D. M. Bailey et al., *Ann. Rpts. Med. Chem* 17, 203 (1982).

RESPIRATORY CONDITIONS

Asthma.

The leukotrienes are potent spasmogens of human trachea, bronchus and lung parenchyma and when administered to normal volunteers as aerosols are 3,800 times more potent than histamine at inducing a 50% decrease in air flow at 30% of vital capacity. They mediate increases in vascular permeability in animals and promote mucous production in human bronchial explants. In addition, Leukotriene $B_4$ may also mediate mucous production and could be an important mediator of neutrophil and eosinophil accumulation in asthmatic lungs. Lipoxygenase products are also thought to be regulators of mast cell degranulation and recent studies with human lung mast cells have suggested that lipoxygenase inhibitors (but not corticosteroids) may suppress antigen induced mast cell degranulation. In vitro studies have shown that antigen challenge of human lung results in the release of leukotrienes and that, in addition, purified human mast cells can produce substantial amounts of leukotrienes. There is therefore good evidence that the leukotrienes are important mediators of human asthma. Lipoxygenase inhibitors would therefore be a new class of drugs for the treatment of asthma. See, for example, B. Samuelsson, *Science*, 220 568–575 (1983).

SKIN DISEASES

Psoriasis.

Psoriasis is a human skin disease which affects between two and six percent of the population. There is no adequate therapy for psoriasis and related skin conditions. The evidence for leukotriene involvement in these diseases is as follows. One of the earliest events in the development of prepapillary lesions is the recruitment of leukocytes to the skin site. Injection of Leukotriene $B_4$ into human skin results in a pronounced neutrophil accumulation. There are gross abnormalities in arachidonic acid metabolism in human psoriatic skin. In particular, highly elevated levels of free arachidonic acid can be measured as well as large amounts of lipoxygenase products. Leukotriene $B_4$ has been detected in psoriatic lesions, but not in noninvolved skin, in biologically significant amounts.

ALLERGIC CONDITIONS

Leukotrienes can be measured in nasal washings from patients with allergic rhinitis and are greatly elevated following antigen challenge. Leukotrienes may mediate this disease through their ability to regulate mast cell degranulation, to modulate mucous production and mucociliary clearance, and to mediate the accumulation of inflammatory leukocytes.

Leukotrienes may also mediate other diseases. These include atopic dermatitis, gouty arthritis, gall bladder spasms and ulcerative colitis. In addition they may have a role in cardiovascular disease because Leukotrienes $C_4$ and $D_4$ act as coronary and cerebral arterial vasoconstrictors and these compounds may also have negative inotropic effects on the myocardium. In addition, the leukotrienes are important mediators of inflammatory disease through their ability to modulate leukocyte and lymphocyte function.

Many substituted di-t-butylphenols are known. Generally these compounds may be useful as antioxidants. Some of these compounds are also known to be active antiinflammatory agents. Compounds wherein 2,6-di-t-butylphenol is substituted in the 4 position by an unsubstituted phenyl or certain simply-substituted phenyls are known as antiinflammatory agents. See, for example, U.S. Pat. No. 4,172,151 and references cited therein.

No compounds wherein a 2,6-di-t-butylphenol is substituted in the 4 position by an anilino group wherein such anilino group is substituted by a moiety including carboxy, tetrazolyl or N-methyltetrazolyl are known.

SUMMARY OF THE INVENTION

This invention relates to certain di-t-butylphenols containing an anilino group which in turn contains an acidic group. These compounds are useful as inhibitors of mammalian leukotriene biosynthesis. As such, these compounds are useful therapeutic agents for treating allergic conditions, asthma, cardiovascular disorders and inflammation. Pharmaceutical compositions comprising such compounds, pharmacological methods of using such compounds, and synthetic intermediates for preparing such compounds are also described.

DETAILED DESCRIPTION OF THE INVENTION

The present invention relates to compounds of Formula I:

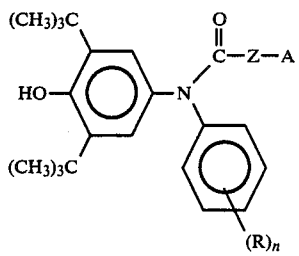

wherein each R independently represents hydrogen, lower alkyl, lower alkoxy, halogen, especially Cl or F, amino, lower alkylamino, lower dialkylamino, hydroxy, lower acylamido, trifluoromethyl, benzoyloxy, carboxy or a carboxy derivative of a compound wherein R is carboxy selected from a lower alkyl carboxylate ester, a (lower)alkylamino(lower)alkyl ester, a pharmaceutically acceptable (lower)alkylamino(lower)alkyl ester acid-addition salt, and a pharmaceutically acceptable carboxylate salt; n is 0, 1, 2 or 3, with the proviso that if n is 2 or 3, only one R substituent, at the most, is carboxy, and further with the proviso that if n is 2 or 3, all R substituents combined contain no more than 6 carbon atoms; Z is a carbon-carbon bond, divalent alkyl of 1 to about 8 carbon atoms and divalent alkylene of 2 to about 8 carbon atoms, and when alkyl or alkylene, Z may optionally be substituted by methyl or phenyl and may contain an ether, thioether or phenylene linkage; A is selected from carboxyl, tetrazolyl and N-methyltetrazolyl, with the proviso that if Z is a carbon-carbon bond, A is carboxyl; and derivatives of the foregoing selected from lower alkyl carboxylate esters, (lower)alkylamino(lower)alkyl esters, pharmaceutically-acceptable (lower)alkylamino(lower)alkyl ester acid-addition salts and pharmaceutically acceptable carboxylate salts of the carboxy moiety when A is carboxyl, and selected from pharmaceutically acceptable alkali metal and alkaline earth salts of the tetrazolyl moiety when A is tetrazolyl.

In the compounds of Formula I wherein A is tetrazolyl, two tautomeric forms of tetrazolyl exist as is known to those skilled in the art. Tautomerism does not exist in tetrazolyl moieties wherein the tetrazolyl ring is substituted on a nitrogen atom by methyl. Instead two N-methyl isomers are obtained, one in which the methyl group is on the 1-position, the other in which it is on the 2-position. All such tautomers and isomers are within the scope of this invention.

The term "lower" as used in connection with alkyl, alkoxy and acylamido denotes straight and branched-chain moieties containing one to about 4 carbon atoms. The preferred lower alkyl and lower alkoxy moieties contain one or two carbon atoms.

Presently preferred compounds of Formula I are those wherein A is carboxyl.

Another presently preferred class of compounds are those wherein R is carboxy.

Preferred compounds of Formula I are those wherein R is hydrogen.

It is well known to the art that pharmaceutically acceptable salts such as alkali metal, alkaline earth, aluminum and other metal and amine salts of pharmaceutically active carboxylic acids are the equivalents of the acids in terms of activity, and in some cases may even offer advantages in absorption, formulation and like. Pharmaceutically-acceptable carboxylate salts of the compounds of the invention which contain carboxyl as A are prepared in an inert atmosphere by reaction of the acid with a base and subsequent evaportion to dryness, preferably under mild conditions. The base may be organic, e.g., sodium methoxide or an amine, or inorganic, e.g., sodium hydroxide. Alternatively, the cation of a carboxylate salt, e.g., sodium, may be displaced by a second cation such as calcium or magnesium when the salt of the second cation is more insoluble in a selected solvent.

Other useful derivatives of the compounds of the invention which contain carboxyl as A include alkyl esters, and alkylaminoalkyl esters, and salts of the latter. In the ester derivatives, the hydrogen portion of the carboxylic acid group is replaced with an alkyl or substituted alkyl, preferably an alkylaminoalkyl group.

Esters of the compounds of the invention may be obtained as intermediates during the preparation of the acidic compound. In some cases, the esters may be prepared directly using standard synthetic methods. These esters may exhibit antiallergic activity, but they are primarily of interest as synthetic intermediates, although in some instances hydrolyzable or salt-forming esters may be of interest as therapeutic agents. Preferred esters are alkyl esters and alkylaminoalkyl esters having one to four carbon atoms in the alkyl group. Especially preferred are alkylaminoalkyl esters such as the dimethylaminoethyl esters which will form salts, e.g., hydrochlorides.

Ester derivatives may be obtained by alkylation of an alkali metal salt of the compound in dimethylformamide with an alkyl iodide or dialkylaminoalkyl chloride.

Pharmaceutically acceptable alkali metal and alkaline earth salts may also be prepared of compounds of Formula I wherein A is tetrazolyl by methods known to those skilled in the art.

Compounds of the invention may be prepared according to the method of Scheme 1 wherein R, n, Z and A are as defined above.

Scheme 1

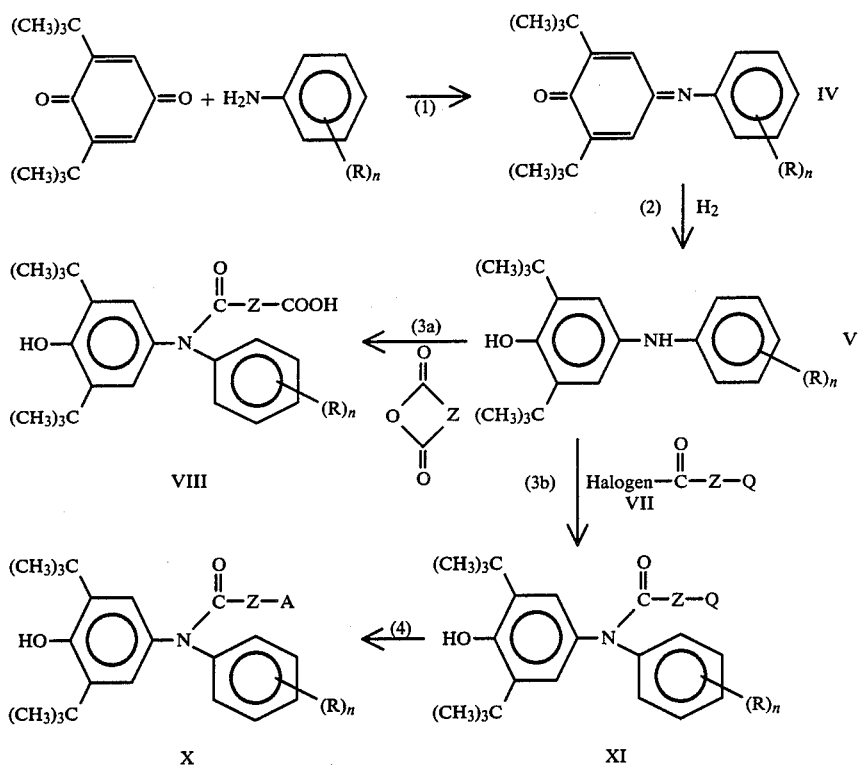

The reaction of step (1) is a Lewis acid catalyzed condensation of the known compound 3,5-di-t-butyl-1,4-p-benzoquinone (II) and an aromatic amine of Formula III. Suitable aromatic amines are known compounds such as aminobenzoic acids, for example 3-aminobenzoic acid and 4-aminobenzoic acid; 3,4-dimethoxyaniline, 4-amino-2,6-di-t-butylphenol, and the like.

Suitable Lewis acid catalysts include boron trifluoride etherate and the like.

The reaction of step (1) is carried out by combining the reactants in an inert solvent such as tetrahydrofuran and heating gently if necessary. The products of Formula IV are readily isolated and recrystallized from polar solvents.

The reaction of step (2) is a reduction of the imino group of the compound of Formula IV to an amino group. It is readily accomplished using catalytic reduction with hydrogen gas in an inert solvent. It may be carried out under neutral conditions or in the presence of base, for example, an equimolar amount of base. Suitable catalysts include platinum or palladium on charcoal. Chemical methods such as reduction by zinc in methanolic hydrochloric acid, zinc in acetic acid or sodium thiosulfate in alkaline medium may also used. The product of step (2) is an intermediate of Formula V.

The reaction of steps (3a) and (3b) is the reaction of the diarylamine of Formula V with either a lactone of Formula VI or an organic halide of Formula VII wherein Y and Z are as defined above and Q is a group which may be readily converted to the desired acidic group, for example, Q being a nitrile or a carboxylate ester. The reaction is carried out by combining the reactants either neat or in an inert solvent, and heating to provide compounds of Formula VIII and Formula IX. Step (3b) is preferred for compounds wherein A is tetrazolyl or N-methyltetrazolyl, or wherein Z is a relatively long hydrocarbon chain.

The reaction of step (4) is the conversion of Q of the compound of Formula IX to the desired acidic group by conventional means, for example, saponification of an ester to the acid or hydrolysis of a nitrile to an acid or conversion of a nitrile to a tetrazole.

Compounds of Formula I wherein A is N-methyltetrazolyl are preferably prepared by alkylating an alkali metal salt of the corresponding compound of Formula I wherein A is tetrazolyl with methyl iodide.

The antiallergic biological activity of the compounds of Formula I generally may be demonstrated via a variety of assays including in vitro assays for measuring inhibition of lipoxygenase activity and leukotriene synthesis, and in vivo assays for inhibiting broncho-constriction. However, since certain of the compounds of Formula I may be prodrugs of antiallergic compounds disclosed in copending U.S. Ser. No. 879,365, filed June 7, 1986 and commonly assigned, incorporated herein by reference, biological activity of the compounds of this invention is sometimes best demonstrated in an in vivo assay such as the aforementioned. As an example of this postulated prodrug-drug relationship, N-(3-carboxyphenyl)-N-(3,5-di-tertiary-butyl-4-hydroxyphenyl)succinamic acid is believed to possibly be a prodrug of 3-(3,5-di-tertiary-butyl-4-hydroxyanilino)benzoic acid which is disclosed in said copending application U.S. Ser. No. 879,365.

More specifically, a suitable assay for demonstrating inhibition of lipoxygenase activity by the compounds of Formula I utilizes lipoxygenase isolated from mammalian lung tissue, for example, the lung tissue of guinea pigs. An example of such an assay is that described by Ben Aziz, et al., Anal. Biochem. 34, 88 (1970), incorporated herein by reference. The inhibition of lipoxygenase activity is measured by a rapid and sensitive spectrophotometric technique. Compounds of Formula I exhibit an $IC_{50}$ (concentration at which 50% of the enzymatic activity is inhibited) of less than about 100 micromolar. Preferred compounds exhibit an $IC_{50}$ of less than about 50 micromolar.

The activity of the compounds of Formula I may also be demonstrated in a more specific test for leukotriene inhibition. This test utilizes the cell free leukotriene biosynthesis system of M. Steinhoff et al. Biochim. Biophys. Acta. 68, 28 (1980), incorporated herein by reference, which consists of homogenized rat basophil leukemia cells. Leukotriene synthesis is initiated by the addition of arachidonate. Solutions are centrifuged and supernatants assayed using a radioimmunoassay developed as described by Aeringhaus et al., FEBS Letter 146, 111–114, incorporated herein by reference. Drugs are dissolved in ethanol or dimethyl sulfoxide and preincubated for five minutes. Phenidone is used as a positive control. The compounds of Formula I exhibit an $IC_{50}$ of 100 micromolar or less.

The compounds of Formula I are relatively inactive as inhibitors of cyclooxygenase. This is important in order for there to be good in vivo antiallergic activity. A convenient in vitro method for measuring cyclooxygenase inhibition is an assay wherein the amount of thromboxane B2 production is measured in a whole human blood clotting assay. The thromboxane B2 production is measured by a radioimmunassay as described by Patrono et al., Thromb. Res. 17, 317 (1980), incorporated herein by reference. The compounds of Formula I do not show appreciable activity at concentrations of 100 micromolar when tested in this assay.

The in vivo test used to demonstrate antiallergic activity of the compounds of Formula I may be any of those known to those skilled in the art. Preferably, bronchoconstriction in sensitized guinea pigs is measured upon antigen challenge. This test is described in broad terms by Piechuta et al., Immunology, 38, 385 (1979), incorporated herein by reference, and more specifically by Hammerbeck and Swingle, Int. Archs. Allergy Appl. Immun. 74, 84–90 (1984), incorporated herein by reference. It is used in a modified form as follows: Male Hartley guinea pigs (250–600 g) which are pretreated with an antihistamine, for example, chlorpheniramine, and then dosed intraperitoneally with a compound of the invention at a level of about 1 to 40 mg/kg 15 minutes prior to challenge or orally at the same dose 30 minutes prior to challenge, are aerosol challenged with either water or ovalbumin at a concentration of 10 mg per ml. The animals are placed under an inverted dessicator jar (18×14 cm) with a constant flow of air coming into the chamber from a compressed-air source to prevent hypoxia. Air flow leaving the chamber and fluctuations due to respiration are monitored through a separate outlet with a Fleisch No. 0000 pneumotachograph (available from Beckman Instruments, Inc. Schiller Park, Ill.) coupled to a Beckman Type R dynograph (available from Beckman Instruments, Inc.). Aerosolization through a third outlet is made via a No. 4 DeVilbiss nebulizer (available from The DeVilbiss Company, Somerset, Pa.) for 90 seconds at 150 mm Hg. The characteristic respiratory patterns observed are summations of two air exchange processes occurring simultaneously in the chamber. One exchange process is due to inspiration and expiration of air into and out of the animal, while the other exchange process is due to the air flow into and out of the chamber due to respiratory movements. The tracing obtained is the mechanical representation of the summation of those flows. Superimposed on the tracings is a characteristic spiking ("notching"), which appears to be an exaggerated expiratory movement, the frequency of which correlates with the severity of the bronchoconstrictive reaction. The frequency of notching for 15-minute periods beginning 4 minutes after the beginning of the aerosol challenge is used for comparing various treatments. Effects are considered significant if the t value achieves $p<0.05$. The compounds of Formula I exhibit an intraperitoneal or oral $ED_{40}$ of 100 mg per kg or less when tested in the above model. Preferred compounds exhibit an $ED_{40}$ of 20 mg per kg or less. Most preferred compounds of Formula I exhibit an $ED_{40}$ of 10 mg per kg.

Thus, compounds of Formula I are antiallergic agents exhibiting in vivo activity in mammals. The pharmaceutical compositions of the present invention will contain sufficient compound of Formula I in a dosage form suitable for inhibiting the mammalian biosynthesis of leukotrienes, or for the treatment desired. The effective concentration of the Formula I compound in the composition will vary as required by the mode of adminstration, dosage form, and pharmacological effect and level desired.

For treating pulmonary conditions such as asthma, the mode of administration may be oral, parenteral, by inhalation, by suppository and the like. Suitable oral dosage forms are tablets, elixirs, emulsions, solutions or capsules, including delayed or sustained release dosage forms. Dosage forms for administration by inhalation include aerosols and sprays and will be administered in metered doses if desired.

For treating other allergies or allergic reactions, the compound of Formula I may be administered by any conventional mode, for example, orally, parenterally, topically, subcutaneously, by inhalation and the like. The oral and parenteral dosage forms are as described for pulmonary treatment. The topical application dosage forms include ointments, sprays, controlled release patches, powders, solutions and the like.

For treating inflammation, the mode of administration may be oral, parenteral, by suppository and the like. The various dosage forms are as described above.

For treating skin diseases such as psoriasis, atopic dermatitis and the like, oral, topical or parenteral administration is useful. For topical application to the diseased area salves, patches, controlled release patches, emulsions, etc. are convenient dosage forms.

For treating cardiovascular conditions any suitable mode of administration such as oral or parenteral may be used.

In addition to the common dosage forms listed above, the compounds of Formula I may also be administered for various utilities and indications or for inhibiting leukotriene synthesis by conventional controlled release means and/or delivery devices.

In preparing suitable dosage forms, conventional compounding procedures and ingredients, for example, diluents, carriers, etc. may be used. Examples of suitable solid carriers are lactose, terra alba, sucrose, talc, gelatin, agar, pectin, acacia, magnesium stearate, stearic acid, and the like. Examples of suitable liquid carriers are syrup, peanut oil, olive oil, water, a polyethylene glycol such as "PEG 400" (available from Union Carbide) and the like. Similarly, the carrier or diluent can include any time delay material well known to the art, such as glyceryl monostearate or glyceryl distearate, these being useful alone or, for example, in combination with wax.

The following examples are provided to illustrate the invention, but are not intended to limit the invention.

EXAMPLE 1

Synthesis of
5-(3,5-Di-t-butyl-4-hydroxy-N-phenylanilino)-5-oxopentanoic Acid 1.1 g (0.010 mole) of glutaric anhydride, 3.0 g (0.010 mole) of the known compound 4-anilino-2,6-di-t-butylphenol, and 30 ml of 1,2-dimethoxyethane were combined and heated at reflux for 24 hours. The volume of the reaction was reduced by two-thirds under a stream of nitrogen, and the reaction was heated for another 24 hours. The remaining solvent was removed under vacuum on a rotary evaporator. The resulting solid was recrystallized twice from a mixture of benzene and hexane and then twice from a mixture of ethanol and water to give 0.6 g of off-white crystalline 5-(3,5-di-t-butyl-4-hydroxy-N-phenylanilino)- 5-oxopentanoic acid, m.p. 168°–170° C. Analysis: Calculated for $C_{25}H_{33}NO_4$: % C, 73.0; % H, 8.1; % N, 3.4: Found: % C, 73.2; % H, 8.0; % N, 3.0.

EXAMPLE 2

Synthesis of
4-(3,5-Di-t-butyl-4-hydroxy-N-phenylanilino)-4-oxobutanoic Acid 1.5 g (0.015 mole) of succinic anhydride, 4.5 g (0.010 mole) of 4-anilino-2,6-di-t-butylphenol, and 10 ml of 1,2-dimethoxyethane were combined and heated at reflux for 48 hours. 1.5 g of succinic anhydride and 5 ml of 1,2-dimethoxyethane were added and the reaction was heated for an additional 24 hours. The reaction mixture was cooled in an ice bath. The resulting precipitate was collected, rinsed with a small amount of cold 1,2-dimethoxyethane, and recrystallized from a mixture of ethanol and water to give 3.7 g of off-white 4-(3,5-di-t-butyl-4-hydroxy-N-phenylanilino)-4-oxobutanoic acid, m.p. 205°–208° C. Analysis: Calculated for $C_{24}H_{31}NO_4$: % C, 72.5; % H, 7.9; % N, 3.5: Found: % C, 72.4; % H, 7.8; % N, 3.3.

EXAMPLE 3

Alternate Synthesis of
5-(3,5-Di-t-butyl-4-hydroxy-N-phenylanilino)-5-oxopentanoic Acid 12.0 g (0.038 mole) of 4-anilino-2,6-di-t-butylphenol was added to a 55° C. melt of 12.0 g (0.105 mole) of glutaric anhydride. The reaction warmed to 90° C. during the addition. The reaction was allowed to cool to 50° C., and was then maintained at that temperature for 3 hours. Thereafter, the mixture was heated briefly to 80° C. and allowed to cool to room temperature. The reaction mass was ground to a powder and the powder was heated in water. This cloudy solution was allowed to cool, and was then basified with dilute sodium hydroxide, extracted twice with diethyl ether, and acidified with dilute hydrochloric acid. The resulting precipitate was collected, dried and recrystallized from a mixture of ethanol and water to give 8.9 g of white crystalline 5-(3,5-di-t-butyl-4-hydroxy-N-phenylanilino)-5-oxopentanoic acid, m.p. 168.5°–169° C. Analysis: Calculated for $C_{25}H_{33}NO_4$:% C, 73.0; % H, 8.1; % N, 3.4; Found: % C, 73.6; % H, 8.1; % N, 3.4.

EXAMPLE 4

Preparation of
N-(3,5-Di-t-butyl-4-hydroxyphenyl)-N-phenyl-2-carboxyphenylacetamide A mixture of 5.0 g (0.016 mole) of 4-anilino-2,6-di-t-butylphenol and 6.0 g (0.037 mole) of homophthalic anhydride was heated at 140°–150° C. for 10 minutes. The resulting solid was partitioned between an organic layer (primarily diethyl ether with a small amount of chloroform) and a dilute aqueous sodium hydroxide layer. The aqueous phase was added to dilute aqueous hydrochloric acid, and the mixture was heated on a steam bath to drive off any dissolved ether and to bring the homophthalic acid into solution. The resulting precipitate was collected and dried to give 6.3 g of a light purple solid, m.p. 170°–175° C. This material was recrystallized from ethanol to give 4.9 g of white crystalline N-(3,5-di-t-butyl-4-hydroxyphenyl)-N-phenyl-2-carboxyphenylacetamide, m.p. 182°–183° C. Analysis: Calculated for $C_{29}H_{33}NO_4.C_2H_5OH$: % C, 73.8; % H, 7.6; % N, 2.8 Found: % C, 73.6; % H, 8.0; % N, 2.6.

EXAMPLE 5

Preparation of
N-(3-Carboxyphenyl)-N-(3,5-di-t-butyl-4-hydroxyphenyl)succinamic Acid Under a nitrogen atmosphere, a mixture of 3.0 g (0.0088 mole) of 3-(3,5-di-t-butyl-4-hydroxyanilino)benzoic acid and 9.0 g (0.090 mole) of succinic anhydride was heated at 150° C. for 15 minutes. The reaction mixture was diluted with pyridine (50 ml) and water, and was poured into cold dilute hydrochloric acid. The resulting precipitate was recrystallized from a mixture of 14 ml of ethanol and 22 ml of water to give a white solid. This solid was heated in 70 ml of water to dissolve any succinic acid, and was collected and heated in 40 ml of ethyl acetate. The ethyl acetate solution was filtered to remove a small amount of insoluble material. The ethyl acetate filtrate was concentrated to 20 ml, and was then diluted with 10 ml of hexane. The resulting precipitate was collected and dried to give 1.85 g of white solid N-(3-carboxyphenyl)-N-(3,5-di-t-butyl-4-hydroxyphenyl)succinamic acid, m.p. 182°–183° C. Analysis: Calculated for $C_{25}H_{31}NO_6$: % C, 68.0; % H, 7.1; % N, 3.2; Found: % C, 68.2; % H, 7.1; % N, 3.0.

EXAMPLE 6

Preparation of
4-[N-(3,5-Di-t-butyl-4-hydroxyphenyl)-N-phenylcarbamoyl]-3-methylbutyric Acid Under a nitrogen atmosphere, a mixture of 2.97 g (0.01 mole) of 4-anilino-2,6-di-t-butylphenol and 6.40 g (0.05 mole) of 3-methylglutaric anhydride was heated at 140° C. for 2 hours. After cooling, the reaction mixture was suspended in 10% sodium hydroxide, and acidified with 10% hydrochloric acid. The resulting precipitate was collected, rinsed with water, air dried, and recrystallized twice from a mixture of ethyl acetate and hexane to give a beige solid. This material was purified by silica gel chromatography, eluting with ethyl acetate, followed by trituration with a mixture of ethyl acetate and hexane. The resulting solid was recrystallized from a mixture of ethyl acetate and hexane to give 2.3 g of white solid 4-[N-(3,5-di-t-butyl-4-hydroxyphenyl)-N-phenylcarbamoyl]-3-methylbutyric acid, m.p. 153°–155° C. Analysis: Calculated for $C_{26}H_{35}NO_4$:% C, 73.4; % H, 8.3; % N, 3.3 Found: % C, 73.4; % H, 8.6; % N, 3.1.

EXAMPLE 7

Preparation of
N-(3,5-Di-t-butyl-4-hydroxyphenyl)-N-phenyl-maleamic Acid

Under a nitrogen atmosphere, a mixture of 2.97 g (0.01 mole) of 4-anilino-2,6-di-t-butylphenol and 4.90 g 0.05 mole) of maleic anhydride was heated at 140° C. for 2 hours. The cooled reaction mixture was suspended in 10% sodium hydroxide, and was then acidified with 10% hydrochloric acid. The resulting precipitate was collected, rinsed with water, air dried, and recrystallized from a mixture of ethyl acetate and hexane to give a yellow solid. This material was dissolved in hot ethanol. The ethanol solution was acidified with 6N hydrochloric acid, and then saturated with water. The resulting precipitate was collected, rinsed with water and air dried. This material was purified by silica gel chromatography, eluting with ethyl acetate, followed by recrystallization from a mixture of ethyl acetate and hexane to give 0.5 g of yellow crystalline N-(3,5-di-t-butyl-4-hydroxyphenyl)-N-phenylmaleamic acid, m.p. 154°–157° C. Analysis: Calculated for $C_{25}H_{29}NO_4$:% C, 72.9; % H, 7.9; % N, 3.5. Found: % C, 73.2; % H, 7.7; % N, 3.3.

EXAMPLE 8

Preparation of
3-[N-(3,5-Di-tertiary-butyl-4-hydroxyphenyl)-N-(3-ethoxyphenyl)carbamoyl]propionic Acid A mixture of 22.0 g (0.10 mole) of 3,5-di-tertiary-butyl-p-benzoquinone, 15.1 g (0.11 mole) of m-ethoxyaniline, 125 ml of tetrahydrofuran and 1 ml of boron trifluoride etherate was heated at reflux for about 40 hours. The reaction mixture was evaporated to give an oil which was partitioned between hexane and 10% hydrochloric acid. The hexane phase was dried by filtering through Whatman IPS phase separation filter paper, then evaporated to give a solid. This solid was triturated with hexane, collected, rinsed with hexane, air dried and then recrystallized from ethanol to give a red solid. 1.0 g of this red solid was recrystallized from ethanol to give 0.9 g of red-orange crystalline 2,6-di-tertiary-butyl-4-(3'-ethoxyphenylimino)-2,5-cyclohexadiene-1-one, m.p. 105°–107° C. Calculated for $C_{22}H_{29}NO_2$: % C, 77.8; % H, 8.6; % N, 4.1; Found: % C, 77.4; % H, 8.5; % H, 3.9.

A solution containing 5.0 g (0.0147 mole) of 2,6-di-tertiary-butyl-4-(3-ethoxyphenylimino)-2,5-cyclohexadien-1-one and 0.1 g of 5% palladium on charcoal catalyst in 250 ml of tetrahydrofuran was hydrogenated at 50 psi. The hydrogenation was complete after three hours. The catalyst was removed by filtration and the filtrate was evaporated to give 2,6-di-tertiary-butyl-4-(3'-ethoxyanilino)phenol as an oil. The structure was confirmed by nuclear magnetic resonance spectroscopy.

A mixture of 5 g (0.015 mole) of 2,6-di-tertiarybutyl-4-(3'-ethoxyanilino)phenol and 1.5 g (0.015 mole) of succinic anhydride was heated under a nitrogen atmosphere at 140° C. for two hours. The reaction was cooled to room temperature and the resulting glass was diluted with water. The addition of 100 ml of 10% sodium hydroxide failed to give a solution so the mixture was acidified with 10% hydrochloric acid. The resulting solid was collected and then recrystallized first from a mixture of ethanol and water and then from a mixture of diethyl ether and hexane to give 2.6 g of tan solid 3-[N-(3,5-di-tertiary-butyl-4-hydroxyphenyl)-N-(3-ethoxyphenyl)carbamoyl]propionic acid, m.p. 128°–130° C. Analysis: Calculated for $C_{26}H_{35}NO_5$: % C, 70.7; % H, 8.0; % N, 3.2; Found: % C, 70.5; % H, 7.8; % N, 3.4.

EXAMPLE 9

Preparation of
3-[N-(3,5-Di-tertiary-butyl-4-hydroxyphenyl)-N-(3-ethylphenyl)carbamoyl]propionic Acid A mixture of 22.0 g (0.10 mole) of 3,5-di-tertiary-butyl-p-benzoquinone, 13.3 g (0.11 mole) of m-ethylaniline, 125 ml of tetrahydrofuran and 1 ml of boron trifluoride etherate was heated at reflux for 40 hours. The reaction mixture was evaporated to give a dark oil. This oil was partitioned between hexane and 10% hydrochloric acid. The hexane phase was dried by filtration through Watman IPS phase separation filter paper and was then evaporated to give an oil.

A mixture of 30.2 g of the oil from the previous step, 1 liter of ethanol and 1.0 g of 5% palladium on charcoal catalyst was placed on a Paar apparatus (initial pressure of 50 psi). Hydrogen uptake was complete after about thirty minutes. Under a nitrogen atmosphere the reaction mixture was filtered to remove the catalyst and the filter cake was rinsed with deoxygenated ethanol. The filtrate was evaporated and the residue was coevaporated twice with toluene to give 2,6-di-tertiary-butyl-4-(3'-ethylanilino)phenol as a dark oil. The structure was confirmed by nuclear magnetic resonacne spectroscopy.

A mixture of 30.1 g (0.09 mole) of 2,6-di-tertiary-butyl-4-(3,-ethylanilino)phenol and 9.2 g (0.09 mole) of succinic anhydride was heated to a temperature of 190° C. over a period of 45 minutes. The reaction mixture was cooled and was then partitioned between 10% sodium hydroxide and chloroform. The chloroform phase wsa washed with water, and was then dried with magnesium sulfate and evaporated to give an oil. This oil was triturated with hexane to give a solid and the solid was recrystallized twice from hexane to give 1.6 g of a light brown solid. This material was purified by silica gel chromatography, eluting with ethyl acetate, followed by recrystallization from a mixture of ethyl acetate and hexane to give 0.45 g of crystalline 3-[N-(3,5-di-tertiary-butyl-4-hydroxyphenyl)-N-(3-ethylphenyl)carbamoylpropionic acid, m.p. 150°–152° C. Analysis: Calculated for $C_{26}H_{35}NO_4$: C, 73.4; % H, 8.3; % N, 3.3; Found: % C, 73.6; % H, 8.2; % N, 3.3.

EXAMPLE 10

Preparation of
3-[N-(3,5-Di-tertiary-butyl-4-hydroxy-phenyl)-N-(3-chlorophenyl)carbamoyl]propionic Acid A mixture of 22.0 g (0.10 mole) of 3,5-di-tertiary-butyl-p-benzoquinone, 14.0 g (0.11 mole) of m-chloroaniline, 125 ml of tetrahydrofuran and 1 ml of boron trifluoride etherate was heated at reflux for about 40 hours. The reaction mixture was evaporated to give an oil which was partitioned between hexane and 10% hydrochloric acid. The hexane phase was dried by filtration through phase separation filter paper, and was then evaporated to give 22.6 g of a dark oil.

A mixture of 5.4 g of oil from the previous step, 200 ml of ethanol and 0.1 g of 5% palladium on charcoal catalyst was placed on a Paar apparatus (initial pressure of 50 psi). Hydrogen uptake was complete after thirty minutes. Under a nitrogen atmosphere, the reaction was filtered and the filter cake was rinsed with deoxygenated ethanol. Evaporation of the filtrate gave a solid which was recrystallized from hexane to give 2.5 g of off-white 2,6-di-tertiary-butyl-4-(3'-chloroanilino)-phenol, m.p. 110°–111° C. Analysis: Calculated for $C_{20}H_{26}ClNO$: % C, 72.4; % H, 7.9; % N, 4.2; Found: % C, 72.5; % H, 7.8; % N, 4.4.

A mixture of 1.50 g (0.0045 mole) of 2,6-di-tertiary-butyl-4-(3'-chloroanilino)phenol and 0.90 g (0.0090 mole) of succinic anhydride was heated under a nitrogen atmosphere at 140° C. for one hour. The resulting solid was recrystallized once from a mixture of ethanol and water and then twice from a mixture of ethyl acetate and hexane to hydroxyphenyl)-N-(3-chlorophenyl)carbamoyl]propionic acid, m.p. 204°–206° C. Analysis: Calculated for $C_{24}H_{30}ClNO$: % C, 66.7; % H, 7.0; % N, 3.2; Found: % C, 67.1; % H, 7.0; % N, 3.2.

EXAMPLE 11

Preparation of 3-[N-(3,5-Di-tertiary-butyl-4-hydroxyphenyl)-N-(4-benzoyloxyphenyl)carbamoyl]propionic Acid A mixture of 5.5 g (0.025 mole) of 3,5-di-tertiary-butyl-p-benzoquinone, 5.9 g (0.075 mole) of p-benzoyloxyaniline, 50ml of tetrahydrofuran and 0.25 ml of boron trifluoride etherate was heated on a steam cone under a stream of nitrogen for two hours. The residue was taken up in hot hexane. The hexane solution was purified by suction chromatography through silica gel, and was then evaporated to give an orange solid. The solid was recrystallized from hexane to give 8.6 g of orange solid 2,6-di-tertiary-butyl-4-(4'-benzoyloxyphenylimino)-2,5-cyclohexadiene-1-one, m.p. 142°–145° C. Analysis: Calculated for $C_{26}H_{29}NO_3$:% C, 78.0; % H, 7.0; % N, 3.4; Found: % C, 77.6; % H, 7.1; % N, 3.2.

A mixture of 5.0 g of 2,6-di-tertiary-butyl-4(4'-benzoyloxyimino)-2,5-cyclohexadiene-1-one, 200 ml of ethanol and 0.1 g of 10% palladium on charcoal catalyst was placed on a Paar apparatus (initial pressure of 50 psi). Hydrogen uptake ceased after about thirty minutes. Under a nitrogen atmosphere the reaction mixture was filtered to remove the catalyst and the filter cake was rinsed with deoxygenated ethanol. Evaporation of the filtrate gave a solid which was recrystallized from hexane to give 2.4 g of orange crystalline 2,6-di-tertiary-butyl-4-(4'-benzoyloxyanilino)phenol, m.p. 138°–140° C. Analysis: Calculated for $C_{27}H_{31}NO_3$:% C, 77.7; % H, 7.5; % N, 3.4; Found: % C, 77.7; % H, 7.5; % N, 3.2.

A mixture of 2.4 g (0.0057 mole) of 2,6-di-tertiary-butyl-4-(4'-benzoyloxyanilino)phenol and 0.58 g (0.0057 mole) of succinic anhydride was heated under a nitrogen atmosphere at a temperature of about 160° C. for 1.5 hours. The resulting solid was recrystallized from ethyl acetate to give 0.7 g of white solid 3-[N-(3,5-di-tertiary-butyl-4-hydroxyphenyl)-N-(4-benzoyloxyphenyl)carbamoyl]propionic acid, m.p. 131°–132° C. Analysis: Calculated for: $C_{31}H_{35}NO_6$:% C, 71.9; % H, 6.8; % N, 2.7; Found: % C, 72.2; % H, 6.9; % N, 2.6.

What is claimed is:

1. A compound of the formula

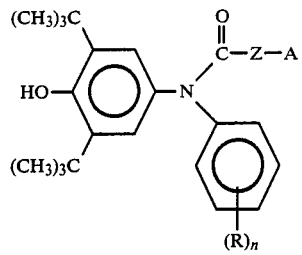

wherein each R independently represents hydrogen, lower alkyl, lower alkoxy, halogen, amino, lower alkylamino, di(lower)alkylamino, hydroxy, lower acylamido, trifluoromethyl, benzoyloxy, carboxy, or a derivative of a compound wherein R is carboxy selected from a lower alkyl carboxylate ester, a (lower)alkylamino(lower)alkyl carboxylate ester, a pharmaceutically acceptable (lower)alkylamino(lower)alkyl ester acid-addition salt, and a pharmaceutically acceptable carboxylate salt; and n is 0, 1, 2 or 3, with the proviso that if n is 2 or 3, only one R substituent, at the most, is selected from carboxy, and further with the proviso that if n is 2 or 3, all R substituents combined contain no more than 6 carbon atoms; Z is a carbon-carbon bond, divalent alkyl of 1 to about 8 carbon atoms or divalent alkylene of 2 to about 8 carbon atoms, and when alkyl or alkylene, Z may optionally be substituted by methyl or phenyl and may contain an ether, thioether or phenylene linkage; A is selected from carboxyl, tetrazolyl, and N-methyl tetrazolyl, with the proviso that if Z is a carbon-carbon bond, A is carboxyl; or a derivative of the foregoing selected from a lower alkyl carboxylate ester, a (lower)alkylamino(lower)alkyl carboxylate ester, a pharmaceutically acceptable (lower)alkylamino(lower)alkyl carboxylate ester acid-addition salt and a pharmaceutically acceptable carboxylate salt of the carboxy moiety when A is carboxyl, and selected from a pharmaceutically acceptable alkali metal and an alkaline earth salt of the tetrazolyl moiety when A is tetrazolyl.

2. A compound according to claim 1, wherein each R is hydrogen.

3. A compound according to claim 1, selected from 5-(3,5-di-t-butyl-4-hydroxy-N-phenylanilino)-5-oxopentanoic acid, 4-(3,5-di-t-butyl-4-hydroxy-N-phenylanilino)-4-oxobutanoic acid, N-(3,5-di-t-butyl-4-hydroxyphenyl)-N-phenyl-2-carboxyphenylacetamide, N-(3-carboxyphenyl)-N-(3,5-di-t-butyl-4-hydroxyphenyl)-succinamic acid, 4-[N-(3,5-di-t-butyl-4-hydroxyphenyl)-N-phenylcarbamoyl]-3-methylbutyric acid, and N-(3,5-di-t-butyl-4-hydroxyphenyl)-N-phenylmaleamic acid.

4. An antiallergic pharmaceutical composition comprising a compound according to claim 1 and a pharmaceutically acceptable vehicle, said compound being present in an amount effective for obtaining an antiallergic response in a mammal.

5. A method for inhibiting bronchoconstriction due to an allergic response in a mammal wherein a compound according to claim 1 is administered to said mammal in an amount effective for obtaining such inhibition.

6. A method according to claim 5, wherein said compound is administered by inhalation.

7. A method according to claim 5, wherein said compound is administered orally.

8. A method for inhibiting leukotriene synthesis in a mammal comprising administering to said mammal a compound according to claim 1 in an amount effective to inhibit said synthesis.

9. A method for inhibiting lipoxygenase activity in a mammal comprising administering to said mammal a compound according to claim 1 in an amount effective to inhibit said activity.

* * * * *

UNITED STATES PATENT AND TRADEMARK OFFICE
CERTIFICATE OF CORRECTION

PATENT NO. : 4,716,178

DATED : December 29, 1987

INVENTOR(S) : Scherrer, et al

It is certified that error appears in the above-identified patent and that said Letters Patent is hereby corrected as shown below:

Col. 12, line 55    Patent:    C, 73.4;
                          Should be:  %C, 73.4;

Col. 13, line 20-22 Patent: --ethyl acetate and hexane to hydroxyphenyl)-N-(3-chlorophenyl)--

Should be: ethyl acetate and hexane to give 0.55g of white solid 3-[N-(3,5-di-tertiary-butyl-4-hydroxyphenyl)-N-(3-chlorophenyl) --

Signed and Sealed this

Twenty-seventh Day of June, 1989

Attest:

DONALD J. QUIGG

Attesting Officer            Commissioner of Patents and Trademarks